(12) United States Patent
Gollier et al.

(10) Patent No.: US 7,629,173 B2
(45) Date of Patent: Dec. 8, 2009

(54) OPTICAL READER SYSTEM AND METHOD FOR MONITORING AND CORRECTING LATERAL AND ANGULAR MISALIGNMENTS OF LABEL INDEPENDENT BIOSENSORS

(75) Inventors: Jacques Gollier, Painted Post, NY (US); Garrett A. Piech, Horseheads, NY (US); Michael B. Webb, Lindley, NY (US)

(73) Assignee: Corning Incorporated, Corning, NY (US)

(*) Notice: Subject to any disclaimer, the term of this patent is extended or adjusted under 35 U.S.C. 154(b) by 90 days.

(21) Appl. No.: 11/210,920

(22) Filed: Aug. 23, 2005

(65) Prior Publication Data

US 2006/0139641 A1 Jun. 29, 2006

Related U.S. Application Data

(63) Continuation-in-part of application No. 11/027,547, filed on Dec. 29, 2004.

(51) Int. Cl.
| | |
|---|---|
| G01N 21/00 | (2006.01) |
| G01N 21/03 | (2006.01) |
| G01N 33/53 | (2006.01) |
| G01N 33/543 | (2006.01) |
| G01N 33/551 | (2006.01) |
| G01N 33/553 | (2006.01) |
| C12M 1/36 | (2006.01) |
| C12M 1/34 | (2006.01) |
| C12M 3/00 | (2006.01) |
| C12Q 1/00 | (2006.01) |

(52) U.S. Cl. .................... 436/164; 435/4; 435/7.1; 435/286.1; 435/286.2; 435/287.1; 435/288.4; 435/288.7; 436/518; 436/524; 436/525; 436/165

(58) Field of Classification Search .............. 435/4, 435/7.1, 286.1, 286.2, 287.1, 288.4, 288.7; 436/518, 524, 525, 164, 165

See application file for complete search history.

(56) References Cited

U.S. PATENT DOCUMENTS

| | | | |
|---|---|---|---|
| 4,710,031 A | 12/1987 | Kelly et al. | 356/440 |
| 4,815,843 A | 3/1989 | Tiefenthaler et al. | 356/128 |
| 4,992,385 A | 2/1991 | Godfrey | 436/525 |
| 5,047,651 A | 9/1991 | Wessner et al. | 250/548 |
| 5,310,686 A | 5/1994 | Sawyers et al. | 436/518 |
| 5,340,715 A | 8/1994 | Slovacek et al. | 435/6 |
| 5,592,289 A * | 1/1997 | Norris | 356/244 |
| 5,631,170 A | 5/1997 | Attridge | 436/518 |

(Continued)

FOREIGN PATENT DOCUMENTS

EP 0 202 021 11/1986

OTHER PUBLICATIONS

J. Dübendorfer et al., "Sensing and Reference Pads For Integrated Optical Immunosensors", Journal of Biomedical Optics, vol. 2, No. 4, Oct. 1997, pp. 391-400.

(Continued)

Primary Examiner—Bao-Thuy L Nguyen
Assistant Examiner—Jacqueline Diramio
(74) Attorney, Agent, or Firm—Timothy M. Schaeberle; Thomas R. Beall; William J. Tucker

(57) ABSTRACT

An optical reader system and method are described herein that can detect a lateral and/or angular misalignment of one or more biosensors so that the biosensors can be properly re-located after being removed from and then reinserted into the optical reader system. In one embodiment, the biosensors are incorporated within the wells of a microplate.

12 Claims, 7 Drawing Sheets

U.S. PATENT DOCUMENTS

| | | | | |
|---|---|---|---|---|
| 5,738,825 | A | 4/1998 | Rudigier et al. | 422/82.11 |
| 5,822,073 | A | 10/1998 | Yee et al. | 356/445 |
| 6,258,326 | B1 * | 7/2001 | Modlin | 422/102 |
| 6,312,961 | B1 | 11/2001 | Voirin et al. | 436/518 |
| 6,346,376 | B1 | 2/2002 | Sigrist et al. | 435/5 |
| 6,455,004 | B1 | 9/2002 | Tiefenthaler | 422/91 |
| 6,709,869 | B2 | 3/2004 | Mian et al. | 436/45 |
| 6,738,141 | B1 | 5/2004 | Thirstrup | 356/445 |
| 6,787,110 | B2 | 9/2004 | Tiefenthaler | 422/91 |
| 6,829,073 | B1 | 12/2004 | Krol et al. | 359/263 |
| 6,884,628 | B2 | 4/2005 | Hubbell et al. | 436/518 |
| 7,057,720 | B2 | 6/2006 | Caracci et al. | 356/300 |
| 2002/0009391 | A1 | 1/2002 | Marquiss et al. | 422/63 |
| 2002/0090320 | A1 | 7/2002 | Burow et al. | 422/64 |
| 2002/0127565 | A1 | 9/2002 | Cunningham et al. | 435/6 |
| 2002/0132261 | A1 | 9/2002 | Dorsel et al. | 435/6 |
| 2002/0168295 | A1 | 11/2002 | Cunningham et al. | 422/82.05 |
| 2003/0007896 | A1 | 1/2003 | Tiefenthaler | 422/91 |
| 2003/0017580 | A1 | 1/2003 | Cunningham et al. | 435/287.2 |
| 2003/0017581 | A1 | 1/2003 | Li et al. | 435/287.2 |
| 2003/0026891 | A1 | 2/2003 | Qiu et al. | 427/58 |
| 2003/0027327 | A1 | 2/2003 | Cunningham et al. | 435/287.2 |
| 2003/0027328 | A1 | 2/2003 | Cunningham et al. | 435/287.2 |
| 2003/0032039 | A1 | 2/2003 | Cunningham et al. | 435/6 |
| 2003/0059855 | A1 | 3/2003 | Cunningham et al. | 435/7.9 |
| 2003/0067612 | A1 | 4/2003 | Ivarsson | 356/600 |
| 2003/0068657 | A1 | 4/2003 | Lin et al. | 435/7.9 |
| 2003/0077660 | A1 | 4/2003 | Pien et al. | 435/7.1 |
| 2003/0092075 | A1 | 5/2003 | Pepper | 435/7.9 |
| 2003/0113766 | A1 | 6/2003 | Pepper et al. | 435/6 |
| 2003/0133640 | A1 | 7/2003 | Tiefenthaler | 385/12 |
| 2003/0169417 | A1 | 9/2003 | Atkinson et al. | 356/135 |
| 2003/0219809 | A1 | 11/2003 | Chen et al. | 435/6 |
| 2004/0091397 | A1 | 5/2004 | Picard | 422/99 |
| 2004/0132172 | A1 | 7/2004 | Cunningham et al. | 435/287.2 |
| 2004/0132214 | A1 | 7/2004 | Lin et al. | 436/518 |
| 2004/0132606 | A1 | 7/2004 | Wolff et al. | 501/66 |
| 2004/0151626 | A1 | 8/2004 | Cunningham et al. | 422/58 |
| 2004/0166496 | A1 * | 8/2004 | Leproust et al. | 435/6 |
| 2004/0223881 | A1 | 11/2004 | Cunningham et al. | 422/82.05 |
| 2004/0247486 | A1 | 12/2004 | Tiefenthaler | 422/82.11 |
| 2005/0014135 | A1 | 1/2005 | Hill et al. | 435/5 |
| 2005/0070027 | A1 * | 3/2005 | Gollier et al. | 436/518 |
| 2005/0088648 | A1 * | 4/2005 | Grace et al. | 356/318 |
| 2005/0099622 | A1 | 5/2005 | Caracci et al. | 356/300 |
| 2005/0153290 | A1 | 7/2005 | Van Beuningen | 435/6 |
| 2005/0236554 | A1 | 10/2005 | Fontaine et al. | 250/208.1 |
| 2006/0106557 | A1 | 5/2006 | Fontaine et al. | 702/87 |
| 2006/0141611 | A1 * | 6/2006 | Frutos et al. | 435/287.2 |
| 2007/0020152 | A1 * | 1/2007 | Costello et al. | 422/104 |

OTHER PUBLICATIONS

K. Tiefenthaler et al., "Integrated Optical Switches and Gas Sensors", Optics Letters, vol. 10, No. 4, Apr. 1984, pp. 137-139.

M. Wiki et al., "Wavelength-Interrogated Optical Sensor for Biochemical Applications", Optics Letters, vol. 25, No. 7, Apr. 1, 2000, pp. 463-465.

K. Cottier et al., "Label-Free Highly Sensitive Detection of (Small) Molecules By Wavelength Interrogation of Integrated Optical Chips", Sensors and Actuators B, vol. 91, 2003, pp. 241-251.

K. Tiefenthaler et al., "Sensitivity of Grating Couplers as Integrated-Optical Chemical Sensors", J. Opt. Soc. Am. B., vol. 6, No. 2, Feb. 1989, pp. 209-220.

W. Lukosz, "Integrated Optical Chemical and Direct Biochemical Sensors", Sensors and Actuators B, vol. 29, 1995, pp. 37-50.

M. Wiki et al., "Novel Integrated Optical Sensor Based on a Grating Coupler Triplet", Biosensors & Bioelectronics, vol. 13, 1998, pp. 1181-1185.

M.J. O'Brien II et al., "SPR Biosensors: Simultaneously Removing Thermal and Bulk-Composition Effects", Biosensors & Bioelectronics, vol. 14, 1999, pp. 145-154.

S.J. Caracci et al., "Method for Creating a Reference Region and a Sample Region on a Biosensor and the Resulting Biosensor", U.S. Appl. No. 11/027,509, filed Dec. 29, 2004.

U.S. Appl. No. 11/027,509, S.J. Caracci et al., filed Dec. 29, 2004.

L.G. Mendoza et al., High-Throughput Microarray-Based Enzyme-Linked Immunosorbent Assay (ELISA), BioTechniques, vol. 27, No. 4, 1999, pp. 778-788.

J.X. Huang et al., "High-Throughput Genomic and Proteomic Analysis Using Microarray Technology", Clinical Chemistry, vol. 47, No. 10, pp. 1912-1916.

T. Wilkop et al., "Analysis of μ-Contact Printed Protein Patterns by SPR Imaging with a LED Light Source", Langmuir, 2004, vol. 20, pp. 11141-11148.

S. Joseph et al., "Specific targeting of ultrasound contrast agent (USCA) for diagnostic application: an in vitro feasibility study based on SAW biosensor", Biosensors & Bioelectronics, vol. 20, 2005, pp. 1829-1835.

T.E. Plowman et al., "Multiple-Analyte Fluoroimmunoassay Using an Integrated Optical Waveguide Sensor", Analytical Chemistry 1999, vol. 71, No. 19, Oct. 1, 1999, pp. 4344-4352.

D. Nedelkov et al., "Surface plasmon resonance mass spectrometry: recent progress and outlooks", TRENDS in Biotechnology, vol. 21, No. 7, Jul. 2003, pp. 301-305.

M. Bilban et al., "Normalizing DNA Microarray Data", Curr. Issues Mol. Bol., 2002, vol. 4, pp. 57-64.

Q. Xu et al., "Protein and Chemical Microarrays—Powerful Tools for Proteomics", Journal of Biomedicine and Biotechnology, 2003, vol. 5, pp. 257-266.

S. Venkatasubbarao, "Microarrays—status and prospects", TRENDS in Biotechnology, vol. 22, No. 12, Dec. 2004, pp. 630-637.

M. Schäferling et al., "Protein Microarray Surface Chemistry and Coupling Schemes", Protein Microarray Technology, Jan. 15, 2004, ISBN: 3-527-30597-1, URL:http://www3.interscience.wiley.com/cgi-bin/booktext/107061764/BOOKPDFSTART>, pp. 11-38.

"Hydrodynamic Addressing of Detection Spots in Biacore® S51", Biacore Technology Note 15.

J.X. Huang et al., "High-Throughput Genomic and Proteomic Analysis Using Microarray Technology", Clinical Chemistry, vol. 47, No. 10, pp. 1912-1916, (2001).

Q. Xu et al., "Protein and Chemical Microarrays—Powerful Tools for Proteomics", Journal of Biomedicine and Biotechnology, 2003, vol. 5, pp. 257-266.

"Hydrodynamic Addressing of Detection Spots in Biacore® S51", Biacore Technology Note 15, (2003).

* cited by examiner

\* Units are pm in vertical and mRd in horizontal

OPTICAL READER SYSTEM AND METHOD FOR MONITORING AND CORRECTING LATERAL AND ANGULAR MISALIGNMENTS OF LABEL INDEPENDENT BIOSENSORS

CROSS REFERENCE TO RELATED APPLICATION

This application is a continuation-in-part application of U.S. patent application Ser. No. 11/027,547 filed Dec. 29, 2004 and entitled "Spatially Scanned Optical Reader System and Method for Using Same" the contents of which are hereby incorporated by reference herein.

BACKGROUND OF THE INVENTION

1. Field of the Invention

The present invention relates to an optical reader system and method for detecting a lateral and/or angular misalignment of one or more biosensors so that the biosensors can be properly re-located after being removed from and then reinserted into the optical reader system. In one embodiment, the biosensors are incorporated within the wells of a microplate.

2. Description of Related Art

A major challenge today is to design an optical reader system that can properly re-locate a label independent detection (LID) microplate after it is removed and then reinserted back into the optical reader system. In particular, what is needed is an optical reader system that can detect and correct a lateral and/or angular misalignment of a re-positioned LID microplate. This need and other needs are addressed by the optical reader system and method of the present invention.

BRIEF DESCRIPTION OF THE INVENTION

The present invention includes an optical reader system and method that uses one or more fiducial markings (e.g., position sensors) on a LID microplate to monitor and correct if needed any lateral and/or angular misalignment of the microplate. In one embodiment, the method includes the steps of: (a) placing the microplate onto a translation stage; (b) using one or more fiducial marking(s) on the microplate to determine a first position of the microplate; (c) removing the microplate from the translation stage; (d) re-inserting the microplate back onto the translation stage; (e) using the fiducial marking(s) on the microplate to determine a second position of the microplate; (f) comparing the first position and the second position of the microplate; and (g) if there is a difference between the two positions, then addressing the lateral and/or angular misalignment of the microplate by: (1) moving the translation stage so that the microplate is located at or substantially near to the first position; or (2) not moving the microplate but instead adjusting via software a measured reading (e.g., resonance wavelength) based upon the known position error and a known translation sensitivity. Likewise, steps (a)-(g) could be accomplished by using a stationary holder for the microplate and instead the optical beams can be moved that interrogate the stationary microplate. In another embodiment, the optical reader system can be used to monitor and correct a lateral and/or angular misalignment of a biosensor (which has a fiducial marking) that is not incorporated within a microplate.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Referring to FIGS. 1-11, there are disclosed several diagrams and graphs which are used to help describe the optical reader system 100 and method 1100 of the present invention. As discussed below, the optical reader system 100 is capable of performing two functions: (1) detecting a biological substance 124 (or a biomolecular binding event) on a biosensor 102; and (2) detecting and correcting any lateral and/or angular misalignment of the biosensor 102 which is caused by the removal and subsequent reinsertion of the biosensor 102 into the optical reader system 100. Prior to discussing the second function, a brief description is provided about how the optical reader system 100 can detect a biological substance 124 on the biosensor 102.

Figure 1:
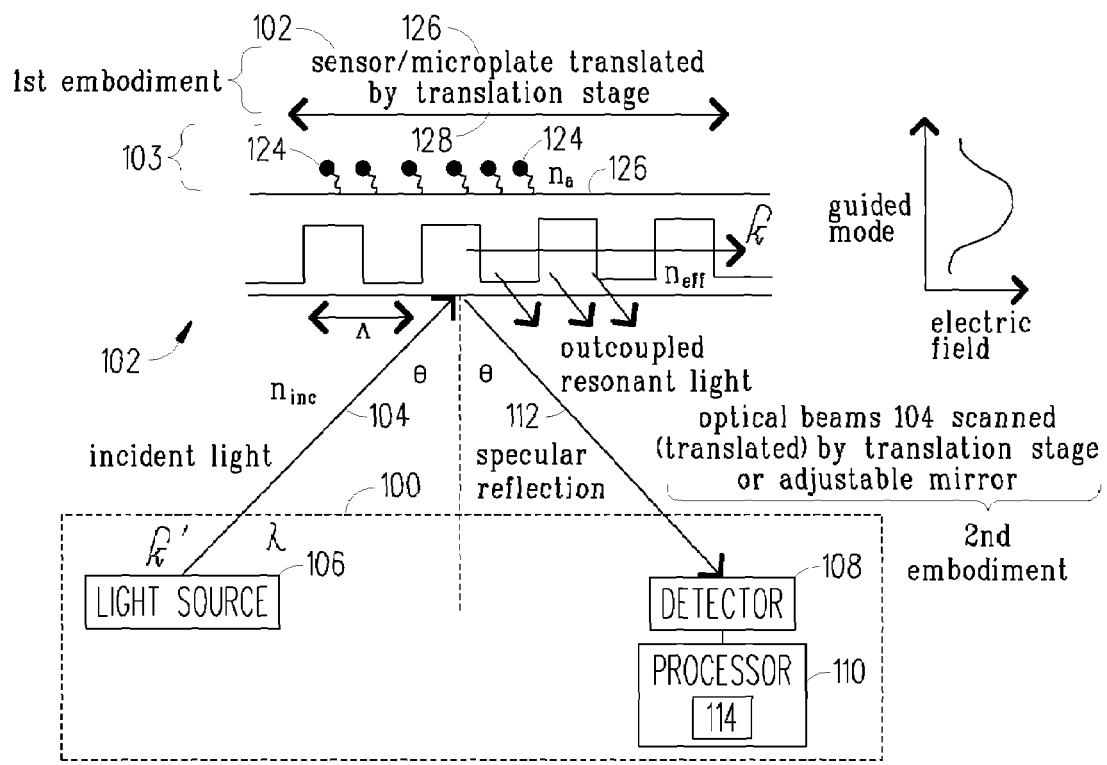
FIG. 1 is a block diagram of an optical reader system that is used to monitor and correct a lateral and/or angular misalignment of a microplate (or biosensor) in accordance with the present invention.

As shown in FIG. 1, the optical reader system 100 is used to interrogate a biosensor 102 (e.g., resonant waveguide grating (RWG) biosensor 102, a surface plasmon resonance (SPR) biosensor 102) to determine if a biological substance 124 is present on the biosensor 102. The optical reader system 100 includes a light source 106 (e.g., lamp, laser, diode) that outputs an optical beam 104 which is scanned across the biosensor 102. Typically, the biosensor 102 is moved so the optical beam 104 can be scanned across the biosensor 102. Alternatively, the optical beam 104 itself may be scanned with a mirror, galvanometer, electro-optic or acousto-optic scanner or other suitable adjustable optical element, across a stationary biosensor 102. While the optical beam 104 is scanned across the biosensor 102, a detector 108 (e.g., spectrometer, CCD camera or other optical detector) collects an optical beam 112 which is reflected from the biosensor 102. A processor 110 (e.g., DSP 110, computer 110) then processes the collected optical beam 112 to obtain and record raw spectral data 114 which is a function of a position (and possibly time) on the biosensor 102. Thereafter, the processor 110 analyzes the raw spectral data 114 to create a spatial map of resonant wavelength (peak position) data which indicates if a biological substance 124 is present on the biosensor 102.

In particular, the biosensor 102 makes use of changes in the refractive index at the sensor surface 126 that affect the waveguide coupling properties of the emitted optical beam 104 and the detected optical beam 112 to enable label-free detection of the biological substance 124 (e.g., cell, molecule, protein, drug, chemical compound, nucleic acid, peptide, carbohydrate) on the superstrate 103 (sensing region) of the biosensor 102. The biological substance 124 may be located within a bulk fluid that is deposited on the superstrate 103 (sensing region) of the biosensor 102 and it is the presence of this biological substance 124 that alters the index of refraction at the surface 126 of the biosensor 102. Thus, to detect the biological substance 124, the biosensor 102 needs to be at least probed with an optical beam 104 and then a reflected optical beam 112 received at the detector 108 is analyzed to determine if there are any changes (~1 part per million) in the refractive index caused by the presence of the biological substance 124. In one embodiment, the top surface 126 may be coated with biochemical compounds (not shown) that only allow surface attachment of specific complementary biological substances 124 which enables a biosensor 102 to be created that is both highly sensitive and highly specific. In this way, the optical reader system 100 and biosensor 102 may be used to detect a wide variety of biological substances 124. And, if multiple biosensors 102 are arranged in array like in a microplate 126 then they may be used to enable high throughput drug or chemical screening studies. For a more detailed discussion about the detection of a biological substance 124 (or a biomolecular binding event) using the scanning optical reader system 100, reference is made to the aforementioned U.S. patent application Ser. No. 11/027,547.

It is well known that when an optical beam 104 is used to interrogate a biosensor 102, then the resonance wavelength often has an undesirable dependence upon the exact spatial location at which the optical beam 104 strikes the biosensor 102. The undesirable variation of the resonance wavelength is often caused by the non-homogeneity of the biosensor 102 which can be attributable to variations in the thickness of the waveguide and/or to variations in the grating period (for example). In fact, a typical variation in the resonance wavelength can be as high as 3 pm per micron. Thus, if one desires to remove and replace the biosensor 102 from the optical reader 100 during the course of an experiment, the biosensor 102 needs to be repositioned to a high accuracy to prevent wavelength shifts induced by translation from overwhelming those wavelength shifts from biochemical binding. The impact, in terms of wavelength shift $\Delta\lambda$ of such a translation sensitivity upon the measurement is thus $$\Delta\lambda = \frac{d\lambda}{dx} \cdot \Delta x.$$

Here $\Delta\lambda/dx$ is the translation sensitivity (pm/μm) and $\Delta x$ is the displacement (μm) of the biosensor 102 between measurements. This formula makes apparent two ways of reducing the impact of translation: 1) reduce the translation sensitivity, $\alpha\lambda/dx$, by careful design of the biosensor 102 and/or the optical reader system 100; or 2) reduce the amount of displacement $\alpha x$ that occurs between measurements.

Figure 2:
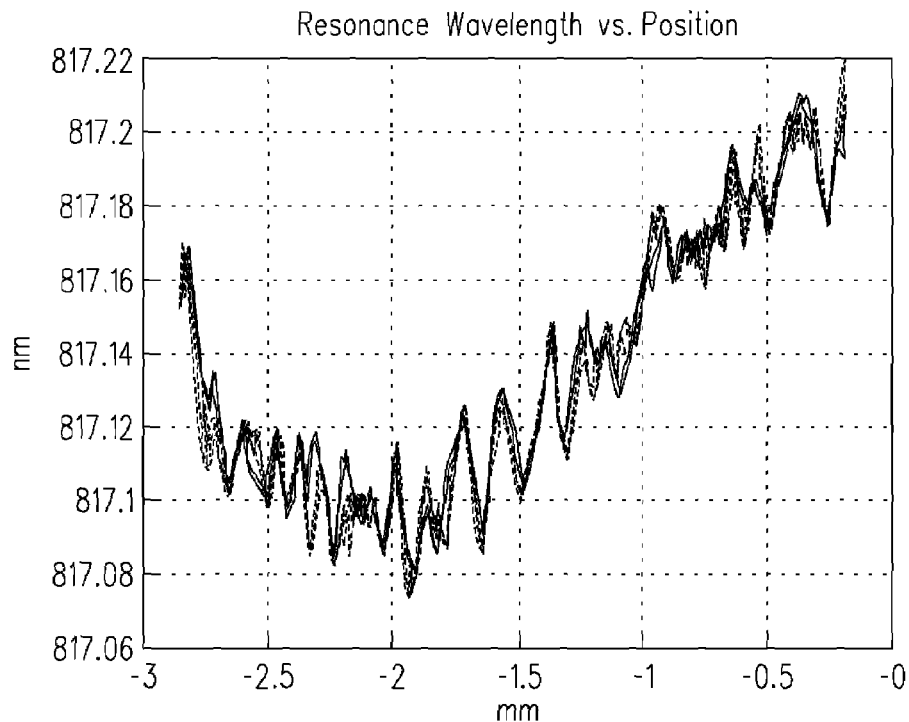
FIG. 2 is a graph that is used to help describe why the optical reader system should monitor and correct the lateral and/or angular misalignment of the microplate (or biosensor) in accordance with the present invention.

To reduce the translation sensitivity, the scanning optical reader system 100 can be used to average these spatial fluctuations in the resonance wavelength. This has been shown to decrease the translational sensitivity by an order of magnitude to around 0.3 pm per micron. FIG. 2 is a graph that shows the typical shape of the resonance wavelength (spectral shift) that can be obtained when scanning one 3 mm long biosensor 102 in one direction with a 100 μm diameter optical beam. It should be appreciated that the use of a "larger" optical beam 104 can help even more by further averaging down high spatial frequency variations. Although, a resonance wavelength translation sensitivity of 0.3 pm per micron works well in many applications, such a sensitivity can still be of great concern for systems attempting to detect small biomolecular binding events. Such small binding events can require resonant wavelength measurement accuracies of better then 0.05 pm. To address this problem one can minimize the translation induced wavelength error by ensuring that the biosensors 102 are properly positioned within the optical reader system 100. This is done by the second function of the optical reader system 100.

A detailed discussion is provided next about three different ways the optical reader system 100 can make sure that the biosensors 102 are properly positioned therein. Basically, the optical reader system 100 can detect and correct a lateral and/or an angular misalignment of the biosensor(s) 102 (microplate 126) by using anyone or a combination of three different types of fiducial markings which can be located on either the biosensor 102 or the microplate 126. The first type of fiducial marking is the edge of the measurement diffraction grating on the biosensor 102 (see FIGS. 3-5 and 6A-6B). The second type of fiducial marking is a non-responding line 602, 602a and 602b located on the measurement diffraction grating of the biosensor 102 (see FIGS. 6C-6D). And, the third type of fiducial marking is a fiducial diffraction grating 702 (position sensor 702) that is separate from the measurement diffraction grating on the biosensor 102 (see FIGS. 7A and 7B). In yet another embodiment, the fiducial marking can be a coating (local metallic, dielectric coating) that is applied to a biosensor 102 or microplate 126. This coating would have a sufficient reflectivity contrast so it could be detected by the optical reader system 100.

Figure 3:
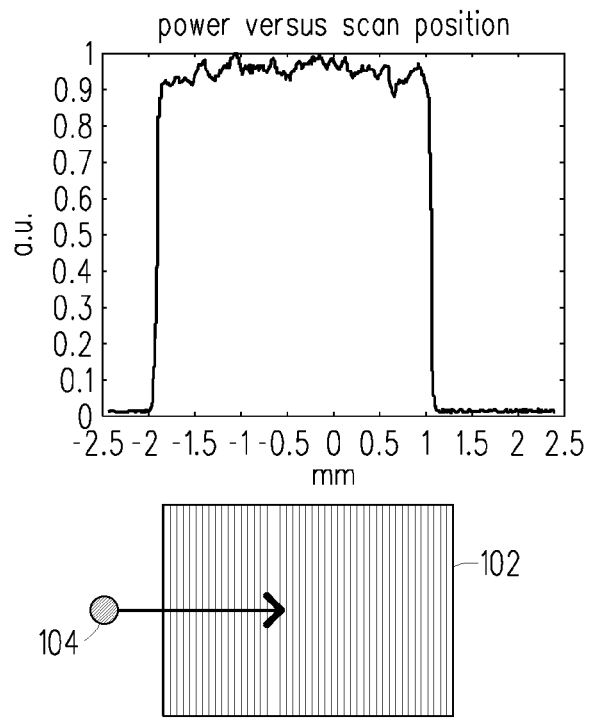
FIGS. 3-5, 6A and 6B are several graphs and diagrams used to help describe one type of fiducial marking that can be formed on the biosensor which enables the optical reader system to monitor and correct the lateral and/or angular misalignment of the microplate (or biosensor) in accordance with the present invention.
Figure 4:
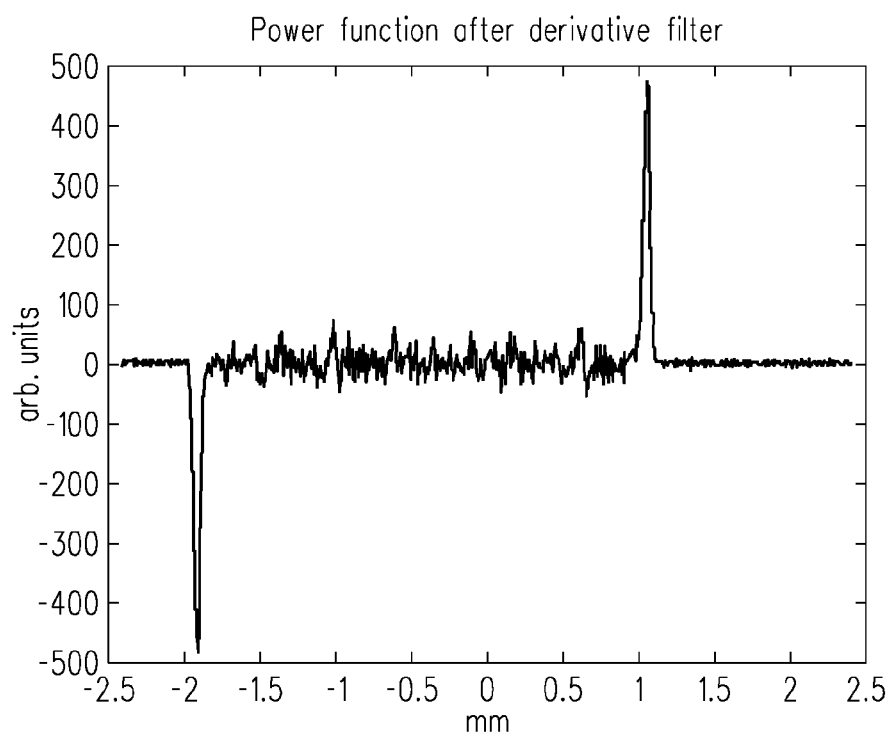

In the first way, the optical reader system 100 scans a biosensor 102 and uses the resulting raw spectral data 114 to create a spatial map of reflected power that enables one to precisely locate the edge of the gratings in the biosensor 102. FIG. 3 is a graph that shows the typical shape to the power evolution of the resonance wavelength when the optical reader system 100 scans a square biosensor 102. To determine the edges of the biosensor 102, various edge detection algorithms can be used. As an example, FIG. 4 is a graph that shows the result of applying a derivative filter on the power profile shown in FIG. 3. By detecting the centroids of the positive and negative peaks of the differentiated signal, one can accurately determine the position of the biosensor 102. Again, in this case the fiducial marking is the edge of the measurement diffraction grating on the biosensor 102.

Figure 5:
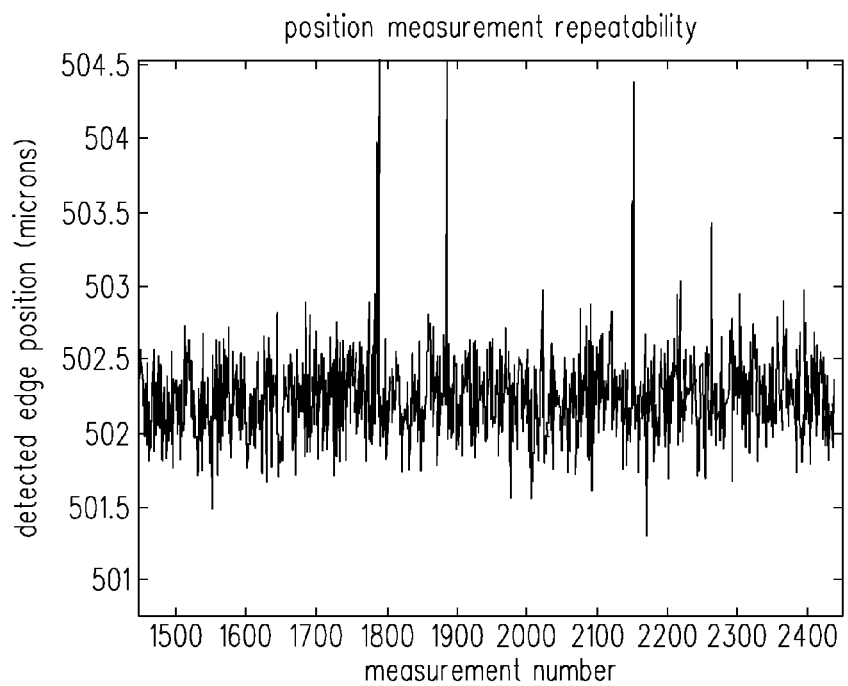

To estimate the repeatability of this type of position measurement, a square biosensor 102 was scanned 500 hundred times. The position of the detected edge then was measured with respect to the position encoder data on a translation stage 128 which supported the biosensor 102 (or microplate 126) (see FIG. 1). Results of this test are shown in FIG. 5. The typical standard deviation of the measurements is in the range of 0.25 microns, which is in fact very close to the resolution of the encoder on the translation stage 128 (see FIG. 1).

This and other types of position measurements are important, because when a microplate 126 which contains an array of biosensors 102 is removed from and then reinserted into the optical reader system 100, one essentially loses track of the absolute translational position of the microplate 126. However, upon reinsertion, when the optical beam 104 is scanned across the microplate 126, by detecting the location where the edges of the grating(s) occur on the biosensor(s) 102, one can "recalibrate" the translation stage 128 (e.g., linear stages 128) so it can very precisely move the microplate 126 back to the same position the microplate 126 was in before it was removed from the optical reader system 100. For a more detailed discussion about how the optical reader system 100 can detect the edges of a measurement diffraction grating in a biosensor 102, reference is made to the aforementioned U.S. patent application Ser. No. 11/027,547.

Additionally, one may use various edge detection concepts to monitor the two dimensional (2D) lateral position of the microplate 126 (see FIGS. 6A-6D). In one such edge detection concept, a square biosensor 102 is scanned in both an x direction and a y direction to determine the lateral 2D position of the microplate 126 (see FIG. 6A). In another edge detection technique, one can scan a triangular biosensor 102 where the x-position is given by the position of the first edge detection and the y-position is given by the distance measured between the two edges detections (see FIG. 6B).

Figure 6A:
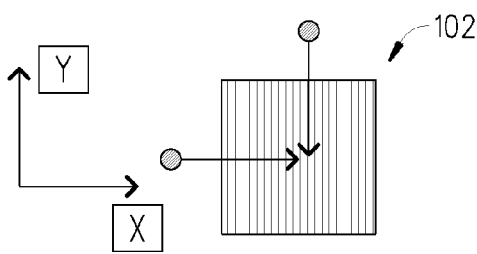
Figure 6B:
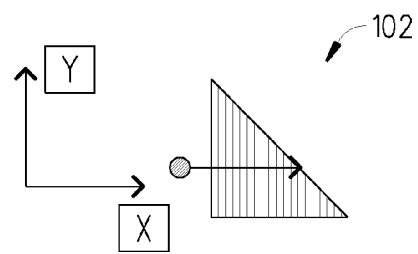
Figure 6C:
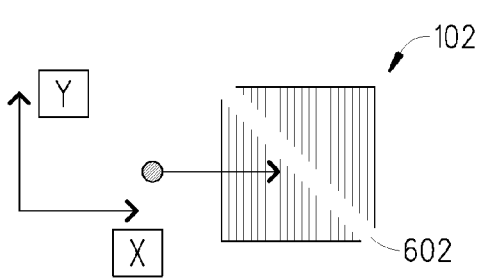
FIGS. 6C and 6D are two diagrams used to help describe a second type of fiducial marking that can be formed on the biosensor which enables the optical reader system to monitor and correct the lateral and/or angular misalignment of the microplate (or biosensor) in accordance with the present invention.
Figure 6D:
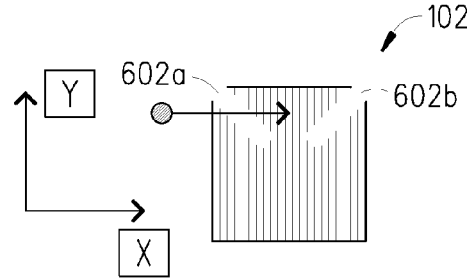

In yet another other edge detection concept, one can use the second type of fiducial marking(s) 602 which are non-responding line(s) 602 located on the biosensor 102 to monitor the lateral 2D position of the microplate 126 (see FIGS. 6C-6D). In one example, the biosensor 102 has a design as shown in FIG. 6C where a non-responding line 602 was made diagonally across the biosensor 102. This diagonal non-responding line 602 enables one to estimate both the x and y positions of the biosensor 102 with a single 1-dimensional beam scan. In particular, when using such a diagonal non-responding line 602 the rising edge of a power vs. position trace is used to determine the x-position and the difference between the rising and falling edges is used to determine the y-position. In yet another example shown in FIG. 6D, the biosensor 102 has two off-center non-responding lines 602a and 602b that are set at the edge of the biosensor 102 which allows one to also use the center portion of the grating to detect a biological substance 124 (or a biomolecular binding event). An advantage of the last example is that one can put fiducial markings 602a and 602b on all of the biosensors 102 which allows one to obtain more data that can be averaged to improve the re-positioning accuracy. However, the drawback of this example is that a complete measurement requires two scanning steps, one scanning step for the position measurement and one scanning step for the biochemical measurement itself. It should be noted that non-responding lines 602, 602a and 602b can be generated by having some areas without a diffraction grating or without a waveguide.

Figure 7A:
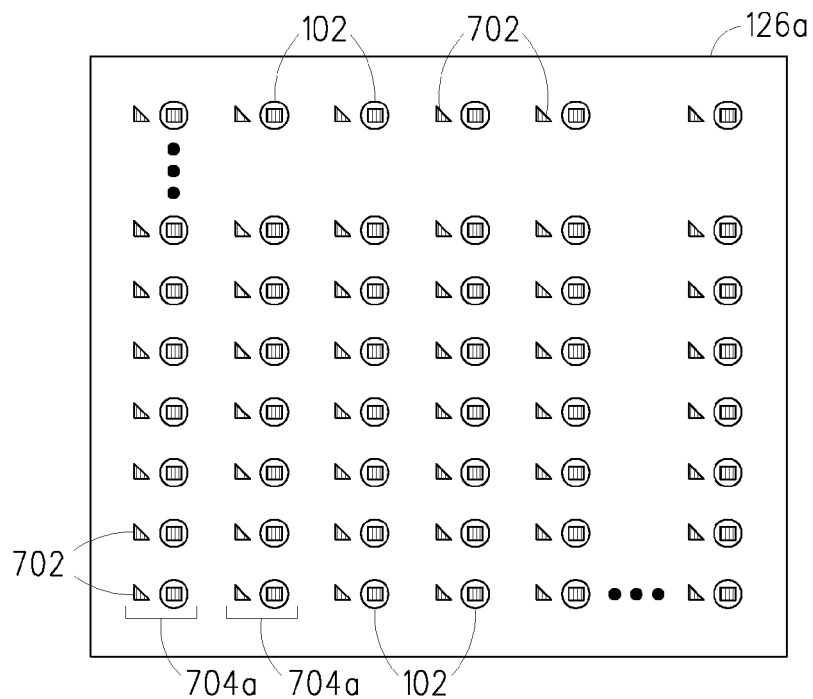
FIGS. 7A and 7B are two diagrams used to help describe a third type of fiducial marking that can be formed on the microplate (or biosensor) which enables the optical reader system to monitor and correct the lateral and/or angular misalignment of the microplate (or biosensor) in accordance with the present invention.
Figure 7B:
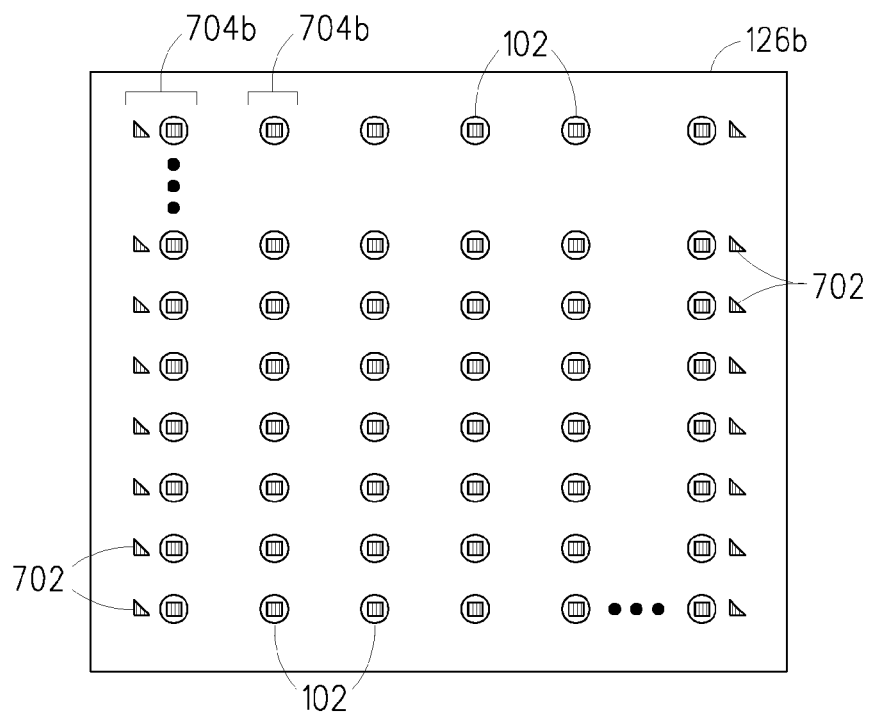

Referring now to the third type of fiducial marking, the optical reader system 100 in this case scans a fiducial diffraction grating 702 (position sensor 702) which is preferably located on a microplate 126 (see FIGS. 7A and 7B). As shown in FIGS. 7A and 7B, the optical reader system 100 can interrogate the fiducial diffraction gratings 702 which are relatively close to the biosensor 102. Then, in real time measure the position of the microplate 126a and 126b and if needed make the translation corrections before the interrogation beam 104 reaches the biosensor 102. This allows continuous scanning with real time position correction.

As can be seen in the exemplary microplates 126a and 126b shown in FIGS. 7A and 7B, one can put a fiducial diffraction grating 702 and a biosensor 102 in each measurement well 704a (see FIG. 7A). Or, one can put a fiducial diffraction grating 702 at the beginning and at the end of the microplate plate 126b (see FIG. 7B). In the last case, the fiducial diffraction gratings 702 are located outside the measurement wells 704b and will be in contact with air or with the glue that holds together the microplate 126. The design of these particular fiducial diffraction gratings 702 in terms of a grating period should be optimized to generate a resonance wavelength close to the one that would be generated if the fiducial diffraction gratings 702 were in contact with the aqueous buffer solutions likely to be used in the wells. This is because the global spectral range of the optical reader system 100 is limited by the spectral width of the light source 106 and detector 108, and it is important to keep the resonance within the operational band of this source/detector system 100.

An advantage of having multiple fiducial diffraction gratings 702 across the microplate 126a and 126b is that one can average the data and obtain a better measurement accuracy. Another advantage of having multiple fiducial diffraction gratings 702 on a microplate 126a and 126b is that it allows one to monitor thermal dilatations of the microplate 126a and 126b. To measure thermal dilations of the microplate 126a and 126b one can optically scan the microplate 126a and 126b and record the locations of the fiducial diffraction gratings 702 (F1, F2, F3 . . . )(or other types of fiducial markings). Then, after some time and possibly a temperature change, one may rescan the microplate 126a and 126b and again record the locations of the same fiducial diffraction gratings 702 (F1, F2, F3 . . . )(or other types of fiducial markings). If the microplate 126a and 126b has grown or shrunk due to temperature change, then the relative locations of the fiducial diffraction gratings 702 (or other types of fiducial markings) will have changed (i.e., $\Delta_{21}$=F2−F1 will have changed, and $\Delta_{31}$=F3−F1 will have changed . . . )

In an alternative embodiment, the fiducial diffraction gratings 702 and the measurement diffraction gratings can have different resonance wavelengths. To have different resonance wavelengths, the fiducial diffraction gratings 702 and the measurement diffraction gratings can be made with different grating periods. Or, they can be made with waveguides that have different thicknesses. In this embodiment, the resonance wavelengths can be detected by measuring the evolution of the power of the two peaks corresponding to the different gratings areas. Then, the edge detection can be made based on the relative power of both peaks.

In yet another embodiment, the fiducial gratings 702 can include features that are perpendicular to the scanning direction of the optical beam and other features that are at a certain angle such as 45 degrees with respect to the scanning direction. In this way, one can determine misalignments in both directions.

Figure 8:
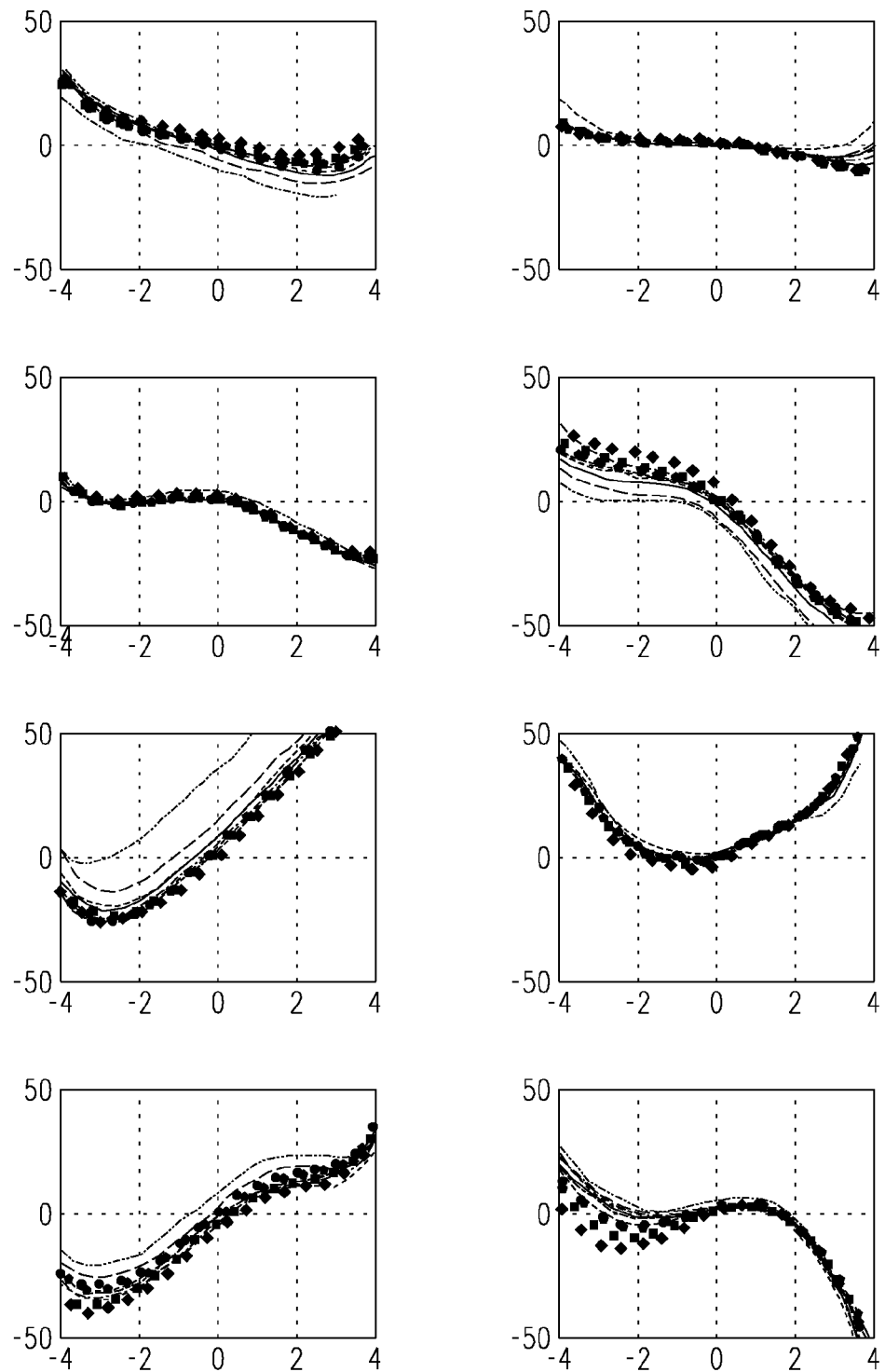
FIGS. 8-10 are three graphs which are used to help explain other uses for the third type of fiducial marking in addition to enabling the optical reader system to monitor and correct the lateral and/or angular misalignment of the microplate (biosensor) in accordance with the present invention.
Figure 9:
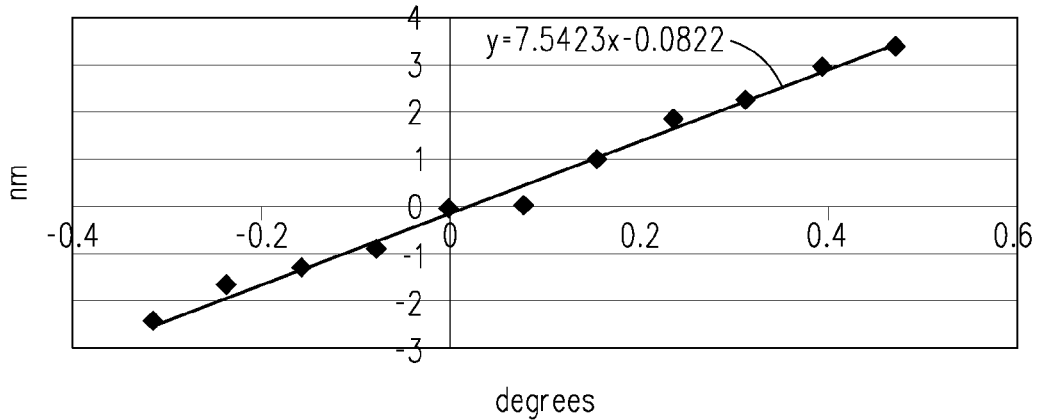

A discussion is provided next about several other uses of the fiducial diffraction gratings 702 (position sensors 702) in addition to their use in helping with the repositioning of the biosensor 102 or microplate 126. When the fiducial diffraction gratings 702 are not in contact with the liquid that is measured in the wells of the microplate 126, then those fiducials are completely isolated and their resonance wavelength is affected only by disturbing external effects such as temperature variations or angular misalignments. As a result, one can use the fiducial diffraction gratings 702 to monitor those external effects as follows:

1. Angular Monitoring—FIG. 8 shows the typical wavelength shift that can be measured as a function of the incidence angle when interrogating biosensors 102 at normal incidence with single mode fibers. As can be seen, the angular sensitivity is in the range of 10 pm/mRd which can make the angle monitoring very critical. One way that this angular variation can be monitored is to interrogate the fiducial diffraction gratings 702 by using a multimode fiber instead of a single mode fiber for the light injection. Indeed, as shown on FIG. 9, when this configuration was tested we obtained angular sensitivities in the range of 432 pm/mRd which is an order of magnitude greater than the sensitivity that obtained with the single mode fibers. So, by comparing the resonance wavelength measured with a multimode fiber and the one measured with the single mode fiber, one can better deduce any angular misalignment of the microplate 126 after reinserting it into the reader 100 by using the multimode fiber.

Figure 10:
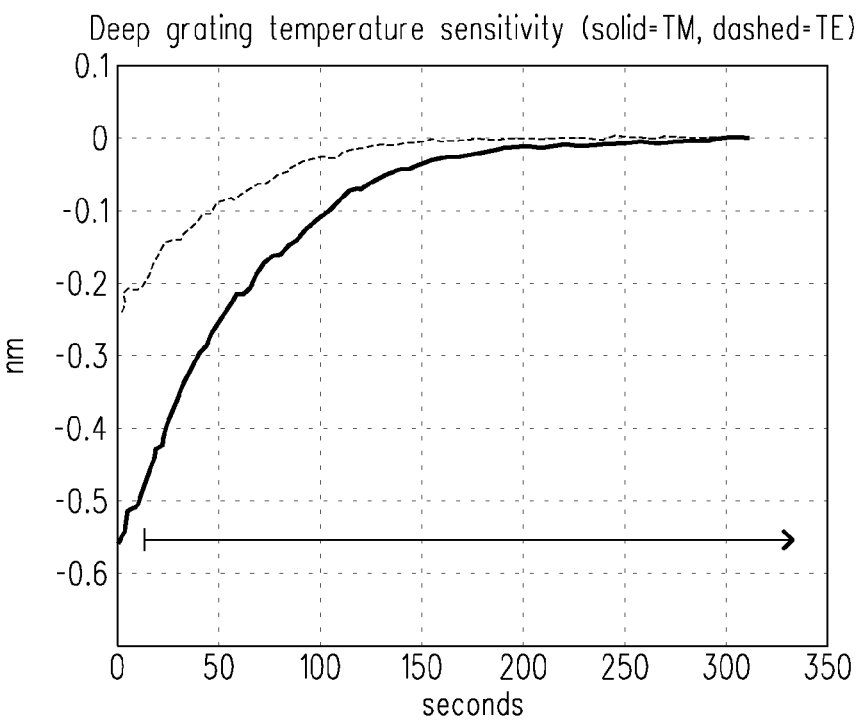

2. Temperature Gradient Monitoring—FIG. 10 is a graph that shows the temperature sensitivity of an interrogated fiducial diffraction grating 702 when the temperature cools by 21° C. As can be calculated from the wavelength changes of the curves shown, the sensitivity coefficients are −10 pm/° C. for TE mode and −26 pm/° C. for the TM mode. Therefore, temperature changes of as small as 0.01° C. can perturb the measured resonance wavelengths by 0.26 pm, which is of significance for small biomolecular binding events. Additionally, even if in-well referencing is used (see U.S. patent application Ser. No. 11/027,509 entitled "Method for Creating a Reference Region and a Sample Region on a Biosensor and the Resulting Biosensor and U.S. patent application Ser. No. 11/027,547 entitled "Spatially Scanned Optical Reader System and Method for Using Same") temperature gradients, and in particular changes in temperature gradients, inside wells may still be large enough to induce resonant wavelength shifts of concern. Assuming that the fiducial diffraction gratings 702 are in contact with glue, then the temperature variation is the major parameter that makes the resonance wavelength fluctuate over time. With this knowledge one can then use the wavelength fluctuations measured across the fiducial diffraction gratings 702 on the microplate 126a and 126b to deduce the temperature gradient fluctuations and check that they are under acceptable levels.

Figure 11:
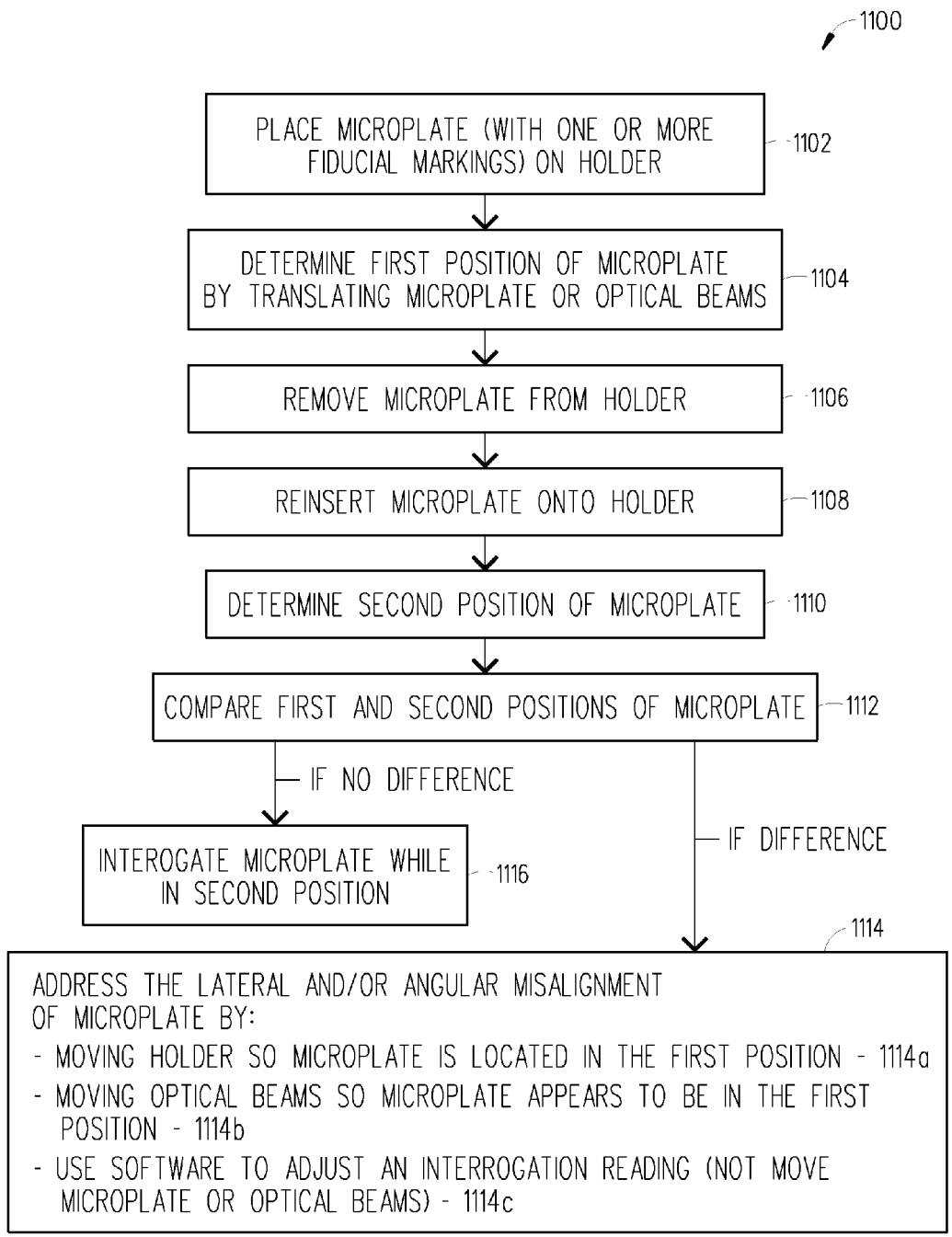
FIG. 11 is a flowchart illustrating the steps of a method for monitoring and correcting a lateral and/or angular misalignment of a microplate (or biosensor) in accordance with the present invention.

From the foregoing, it can be readily appreciated by those skilled in the art that the present invention also includes a method 1100 for monitoring and correcting if needed any lateral and/or angular misalignment of the microplate 126. As shown in the flowchart of FIG. 11, the method 1100 includes the steps of: (a) place microplate (with one or more fiducial markings) on holder which in one embodiment is the translation stage 128 and in another embodiment is a stationary holder (not shown) (step 1102); (b) using one or more fiducial markings on the microplate 126 to determine a first position of the microplate 126 (step 1104); (c) removing the microplate 126 from the holder (step 1106); (d) reinserting the microplate 126 back onto the holder (step 1108); (e) using the fiducial marking(s) on the microplate 126 to determine a second position of the microplate 128 (step 1110); (f) comparing the first position and the second position of the microplate 126 (step 1112); (g) if there is a difference between the two positions, then addressing the lateral and/or angular misalignment of the microplate 126 (step 1114) by: (1) moving the translation stage 128 so that the microplate 126 is located at or substantially near to the first position (step 1114a); or moving the optical beams 104 so that the microplate which is on the stationary holder appears to be in the first position (step 1114b) ; or (3) not moving the microplate 126 or the optical beams 104 but instead adjusting via software a measured interrogation reading (e.g., resonance wavelength) based upon the known position error and a known translation sensitivity (step 1114c); and (h) if there is no difference (or no substantial difference) between the two positions, then interrogate the microplate 126 while it is in the second position (step 1116).

It should be noted that the term angular misalignment as used above is the skew that is caused by the microplate 126 being rotated in the Z axis if the X&Y are the lateral axis. Alternatively, it should be noted that an angular misalignment can also be caused if one performs a "skewed" scan across the microplate 126 where one simultaneously moves the X&Y motion stages in a coordinated skewed motion.

It should also be noted that in most of the drawings herein, were made based on the assumption that the sensor is spectrally interrogated. This means that the sensor is interrogated at a fixed incidence angle with a broad spectral source and that the wavelength is detected in the reflected beam. The source is then a broad spectral source and the detector is a wavelength sensitive detector such as a spectrometer. However, it should be appreciated that the principle of the present invention can also be extended to an angular interrogation approach where the biosensor is interrogated with monochromatic light and then a resonant angle is detected in the reflected beam.

Furthermore, it should be noted that there are configurations of the present invention that do not need to use scanning to position, re-position and/or interrogate the biosensor 102. One such non-scanning system involves the use of a vision system. The vision system would create an image of the biosensor(s) 102, the optical beams 104, and/or the fiducials on a position sensitive detector (e.g., CCD camera). And, this vision system could make use of the fiducials by looking at the position of the fiducials imaged on the CCD camera and then make the appropriate adjustments.

Although multiple embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A method for detecting and correcting a misalignment of a microplate in an optical reader system, said method comprising the steps of:

placing said microplate onto a holder;

scanning a fiducial marking on said microplate to determine a first position of said microplate;

removing said microplate from said holder;

re-inserting said microplate back onto said holder;

scanning said fiducial marking on said microplate to determine a second position of said microplate;

comparing the first position and the second position of said microplate; and if there is a difference between the two positions, then addressing the lateral and/or angular misalignment of said microplate such that the re-inserted microplate is positioned to be located at or substantially near to the first position, wherein the fiducial marking includes features that are at one angle to a scanning direction of an optical beam and features that are at a second angle to the scanning direction of the optical beam which enables one to determine misalignments if any in two directions.

2. The method of claim 1, wherein said addressing step includes the step of moving said holder so that the microplate is located at or substantially near to the first position.

3. The method of claim 1, wherein said addressing step includes the step of moving one or more optical beams used to interrogate said fiducial marking so that the microplate is located at or substantially near to the first position.

4. The method of claim 1, wherein said addressing step includes the step of using software to adjust a measured interrogation reading based upon the known position error and a known translation sensitivity.

5. The method of claim 1, wherein said step of scanning the fiducial marking on said microplate to determine either the first position or the second position of said microplate includes:
generating an optical beam;
scanning the optical beam across said fiducial marking on said microplate;
collecting the scanned optical beam which is reflected from said fiducial marking on said microplate;
processing the collected optical beam to determine either the first position or the second position of said microplate as a function of a position of said holder; and
recording either the first position or the second position of said microplate as a function of the position of said holder.

6. The method of claim 1, further comprising the step of determining whether or not a biological substance is present or a biomolecular event occurred on a surface of a measurement diffraction grating within a well in said microplate.

7. The method of claim 6, wherein said determination of the second position of said microplate and said determination of whether or not a biological substance is present or a biomolecular event occurred within the well in said microplate are performed in one optical beam scanning step.

8. The method of claim 6, wherein said determination of the second position of said microplate and said determination of whether or not a biological substance is present or a biomolecular event occurred within the well in said microplate are performed in two optical beam scanning steps.

9. The method of claim 1, further comprising the step of scanning multiple fiducial markings on said microplate to measure thermal dilations of said microplate.

10. The method of claim 1, further comprising the step of scanning the fiducial marking which is a fiducial diffraction grating to determine a temperature gradient.

11. The method of claim 1, wherein said fiducial marking on said microplate is a fiducial diffraction grating that is separate from a measurement diffraction grating.

12. The method of claim 11, wherein said fiducial diffraction grating is located outside a measurement well which contains the measurement diffraction grating.

* * * * *